(12) United States Patent
Johnston et al.

(10) Patent No.: US 7,784,697 B2
(45) Date of Patent: Aug. 31, 2010

(54) METHODS OF DRIVING A SCANNING BEAM DEVICE TO ACHIEVE HIGH FRAME RATES

(75) Inventors: Richard S Johnston, Sammamish, WA (US); Matthew J Kundrat, Seattle, WA (US); Per G Reinhall, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 11/969,141

(22) Filed: Jan. 3, 2008

(65) Prior Publication Data

US 2008/0218824 A1    Sep. 11, 2008

Related U.S. Application Data

(63) Continuation-in-part of application No. 11/833,831, filed on Aug. 3, 2007, now abandoned, which is a continuation of application No. 11/612,888, filed on Dec. 19, 2006, now Pat. No. 7,252,236, which is a continuation of application No. 11/021,981, filed on Dec. 23, 2004, now Pat. No. 7,159,782.

(51) Int. Cl.
*G02B 5/00* (2006.01)

(52) U.S. Cl. ........... 235/462.32; 359/199; 359/199.1; 359/196; 359/214

(58) Field of Classification Search .......... 235/462.32
See application file for complete search history.

(56) References Cited

U.S. PATENT DOCUMENTS

| | | | |
|---|---|---|---|
| 4,527,893 A | 7/1985 | Taylor | |
| 4,677,683 A | 6/1987 | Pferd et al. | |
| 4,919,508 A | 4/1990 | Grace et al. | |
| 4,991,971 A | 2/1991 | Geary et al. | |
| 5,011,259 A | 4/1991 | Lieber et al. | |
| 5,317,148 A | 5/1994 | Gray et al. | |
| 5,400,267 A | 3/1995 | Denen et al. | |
| 5,625,451 A | 4/1997 | Schiff et al. | |
| 5,681,307 A | 10/1997 | McMahan | |
| 5,693,042 A | 12/1997 | Boiarski et al. | |
| 5,727,098 A | 3/1998 | Jacobson | |
| 5,742,718 A | 4/1998 | Harman et al. | |

(Continued)

FOREIGN PATENT DOCUMENTS

WO    WO 00/75712    12/2000

OTHER PUBLICATIONS

"Engineering Study of an Endoscope Design." *Human Interface Technology*, <www.hitl.washington.edu/research/endoscope/> (Sep. 30, 2004).

(Continued)

*Primary Examiner*—Daniel Walsh
*Assistant Examiner*—Tae Kim
(74) *Attorney, Agent, or Firm*—Townsend & Townsend & Crew LLP

(57) ABSTRACT

The present invention provides methods and systems for scanning an illumination spot over a target area. The present invention removes stored energy from a scanning element to stop the scanning element from vibrating and to substantially return the scanning element to its starting position so as to enable high frame rates.

10 Claims, 7 Drawing Sheets

U.S. PATENT DOCUMENTS

| | | | |
|---|---|---|---|
| 5,764,874 | A | 6/1998 | White |
| 5,768,461 | A | 6/1998 | Svetkoff et al. |
| 5,822,486 | A | 10/1998 | Svetkoff et al. |
| 5,870,511 | A | 2/1999 | Sawatari et al. |
| 5,907,425 | A | 5/1999 | Dickensheets et al. |
| 5,933,240 | A | 8/1999 | Jurca |
| 6,046,720 | A | 4/2000 | Melville et al. |
| 6,091,067 | A | 7/2000 | Drobot et al. |
| 6,211,904 | B1 | 4/2001 | Adair et al. |
| 6,222,628 | B1 | 4/2001 | Corallo et al. |
| 6,327,493 | B1 | 4/2001 | Adair et al. |
| 6,294,775 | B1 | 9/2001 | Seibel et al. |
| 6,329,778 | B1 | 12/2001 | Culp et al. |
| 6,388,641 | B2 | 5/2002 | Tidwell et al. |
| 6,402,743 | B1 | 6/2002 | Orszulak et al. |
| 6,411,838 | B1 | 6/2002 | Nordstrom et al. |
| 6,492,962 | B2 | 12/2002 | Melville et al. |
| 6,563,105 | B2 | 5/2003 | Seibel et al. |
| 6,564,087 | B1 | 5/2003 | Pitris et al. |
| 6,627,903 | B1 | 9/2003 | Hirayanagi |
| 6,666,860 | B1 | 12/2003 | Takahashi |
| 6,713,079 | B2 | 3/2004 | Dvorkis et al. |
| 6,836,560 | B2 | 12/2004 | Emery |
| 6,845,190 | B1 | 1/2005 | Smithwick et al. |
| 6,856,712 | B2 | 2/2005 | Fauver et al. |
| 6,906,739 | B2 | 6/2005 | Suzuki et al. |
| 6,967,772 | B2 | 11/2005 | Harris |
| 6,975,898 | B2 | 12/2005 | Seibel |
| 7,189,961 | B2 | 3/2007 | Johnston et al. |
| 7,298,938 | B2 | 11/2007 | Johnston et al. |
| 7,391,013 | B2 | 6/2008 | Johnston et al. |
| 2001/0030744 | A1 | 10/2001 | Chang |
| 2003/0010826 | A1* | 1/2003 | Dvorkis et al. ......... 235/462.37 |
| 2004/0076319 | A1 | 4/2004 | Fauver et al. |
| 2004/0254474 | A1 | 12/2004 | Seibel et al. |
| 2006/0138238 | A1* | 6/2006 | Johnston et al. ........ 235/462.32 |

OTHER PUBLICATIONS

"Micro-Optical Fabrication of a Fiber Scanning System," *Human Interface Technology*, <www.hitl.washington.edu/projects/mfabfiber/> (Sep. 29, 2004).

"Q Factor" from *Wikipedia, The Free Encyclopedia*, May 20, 2004, <www.en.wikipedia.org/wiki/Q_factor> (Jun. 22, 2004).

Andersen, J. and Seibel, E., "Real-Time Hazard Detection Via Machine Vision for Wearable Low Vision Aids," *5th Intl. Symposium on Wearable Computers, Proceedings of IEEE ISWC*, pp. 182-183 (2001).

Brown, C. et al., "A Novel Design for a Scanning Fiberoptic Endoscope," *Human Interface Technology Laboratory*, University of Washington, Seattle, WA 98195-2142 and *Mechanical Engineering Department*, University of Washington, Seattle, WA 98195.

Brown, C. et al., "Mechanical Design and Analysis for a Scanning Fiber Endoscope," *ASME International Mechanical Engineering Congress and Exposition*, New York, NY, 11-16, BED-vol. 50:165-166 (Nov. 2001).

Fauver, M. et al., "Microfabrication of Fiber Optic Scanners," in Proceedings of Optical Scanning II, *SPIE*, 4773:102-110 (2002).

Johnson, B., "Grating Shrinks Endoscope," *Photonics Spectra*, (Oct. 2003), <www.photonics.com/spectra/applications/QX/ASP/aoaid.335/QX/read.htm> (Sep. 30, 2004).

Johnston, R. et al., U.S. Appl. No. 11/094,017, filed Mar. 29, 2005.

Johnston, R., U.S. Appl. No. 10/956,241, filed Oct. 1, 2004.

Piyawattanametha, W. et al., "A MEMS Non-Interferometric Differential Confocal Scanning Optical Microscope," *Transducers 2001 & Eurosensors XV*, Munich, Germany, 4 pages (Jun. 10-14, 2001).

Seibel, E. and Smithwick, Q., "Single Fiber Flexible Endoscope: General Design for Small Size, High Resolution, and Wide Field of View," *Proceedings of the SPIE, Biomonitoring and Endoscopy Technologies*, 4158:29-39 (2001).

Seibel, E. and Smithwick, Q., "Unique Features of Scanning Fiber Optical Endoscopy," presented at the 2000 Annual Fall Meeting of the Biomedical Engineering Society, BMES, Seattle, WA, *Annals of Biomedical Engineering*, vol. 28, Suppl. 1, S-40 (Oct. 12-14, 2000).

Seibel, E. et al., "Prototype Scanning Fiber Endoscope," presented at *SPIE BiOS*, San Jose, CA (Jan. 2002).

Seven, R., "At the UW Hit Lab, There's Virtue in Virtual Reality," Seattletimes.com, Apr. 11, 2004, <www.seattletimes.nwsource.com/pacificnw/2004/0411/cover.html> (Jun. 9, 2004).

Smithwick, et al., "Modeling and Control of a Resonant Fiber Scanner for Laser Scanning Display or Acquisition," *Department of Aeronautics and Astronautics and Human Interface Technology Laboratory*, University of Washington, PowerPoint presentation (33 pages) (May 22, 2003).

Smithwick, et al., "Modeling and Control of the Resonant Fiber Scanner for Laser Scanning Display or Acquisition," *SID 03 Digest*, 34:1455-1457 (2003).

Smithwick, Q. et al., "Control Aspects of the Single Fiber Scanning Endoscope," Proceedings of SPIE vol. 4253 International Symposium on BiOS, *Optical Fibers and Sensors for Medical Applications*, 4253:176-188 (2001).

Smithwick, Q. et al., "Depth Enhancement Using a Scanning Fiber Optical Endoscope," Optical Biopsy IV, Ed. Robert R. Alfano, *Proc. of SPIE*, vol. 4613:222-233 (2002).

Tearney, G. et al., "Scanning Single-Mode Fiber Optic Catheter-Endoscope for Optical Coherence Tomography," *Optics Letters*, 21(7):543-545 (Apr. 1, 1996).

Wang, W. et al., "Development of an Optical Waveguide Cantilever Scanner," Opto-Ireland 2002: Optics and Photonics Technologies and Applications, *Proc. SPIE*, 4876:72-83 (2003).

Wang, W. et al., "Micromachined Optical Waveguide Cantilever as a Resonant Optical Scanner," *Sensors and Actuators A*, 102:165-175 (2002), Aug. 2002.

* cited by examiner

METHODS OF DRIVING A SCANNING BEAM DEVICE TO ACHIEVE HIGH FRAME RATES

CROSS-REFERENCES TO RELATED APPLICATIONS

The present application is a continuation-in-part of U.S. patent application Ser. No. 11/833,831, filed Aug. 3, 2007, which is a continuation of U.S. patent application Ser. No. 11/612,888, filed Dec. 19, 2006, which is a continuation of U.S. patent application Ser. No. 11/021,981, filed Dec. 23, 2004, the full disclosures of which are incorporated herein by reference.

STATEMENT REGARDING FEDERALLY SPONSORED RESEARCH OR DEVELOPMENT

This invention was made with government support under grant number CA094303-R33 awarded by the National Institutes of Health. The government has certain rights in this invention.

BACKGROUND OF THE INVENTION

The present invention relates generally to methods and scanning beam systems that provide high frame rates. More particularly, the present invention provides methods and systems for removing energy that is stored in a resonant scanning element.

A scanning beam device that has been developed by the University of Washington uses a single optical fiber to scan an illumination spot over a target area in a one or two dimensional scan pattern. Light reflected from the target area is sequentially captured by a light detector, such as a photodetector. The photodetector response is then used to determine the brightness of the small portion of the image that corresponds to the small area illuminated by the illumination spot at that given point in time during the scanning pattern.

While the optical fiber can be driven at any number of frequencies and in any number of one or two dimensional scan patterns, the optical fiber and the illumination spot is typically driven in at resonant frequency of the optical fiber in a spiral shaped scan pattern. "Resonant" is used herein to mean that the optical fiber is driven within a Q-factor of its resonant frequency. When driven within the Q-factor of the resonant frequency (FIG. 3), the optical fiber can achieve its desired deflection while using a minimal amount of energy.

As shown in FIG. 1, in an idealized spiral scan pattern 11 the illumination spot typically starts at an initial, central position and spirals outward until a maximum desired diameter is reached. Once the illumination spot reaches its maximum diameter, it is desirable to return the illumination spot to the center. One proposed spiral scan pattern spirals the illumination spot outward to its maximum diameter, and then spirals the illumination sport inward by retracing the original spiral pattern. Of course, if desired, it may be possible to start the scan pattern at its maximum diameter and then spiral the illumination spot inward toward the middle.

To achieve the resonant spiral scan pattern 11 of FIG. 1, the optical fiber is driven along two drive axes (y and z or horizontal and vertical) with horizontal and vertical triangle amplitude modulated sine waves 13, 15 that are driven with a 90 degree phase shift between them (FIG. 2). If the optical fiber is circular, the horizontal and vertical resonant vibrations will have the same frequency and equal amplitude (but still 90 degrees out of phase). An increasing amplitude portion 17 of the drive signals 13, 15 cause the illumination spot to spiral outward from the initial, central position. The decreasing amplitude portion 19 of the drive signals 13, 15 cause the illumination spot to spiral inward, back toward the initial, central position. It was contemplated that images of the target area could be obtained by collecting back scattered light during the increasing amplitude portion 17, the decreasing amplitude portion 19, or both.

Applicants have found that there are two significant issues when driving a scanning element using the drive signals 13, 15 of FIG. 2.

First, because the scanning element is typically driven substantially in resonance, the scanning element tends to store a large amount of energy. The stored energy will cause the scanning element to continue to move at large amplitudes even after the amplitude of the drive signal is reduced (or removed). For example, in experiments Applicants have found that the illumination spot will follow the increasing amplitude portion 17 of the drive signal rather closely, but when the drive signal moves to the decreasing amplitude portion 19, the illumination spot does not follow as closely. Instead, the stored energy in the scanning element causes the illumination spot to decrease its scan diameter at a much lower rate than the drive signal.

While image and drive remapping methods (described in commonly owned and copending U.S. patent application Ser. No. 10/956,241, filed Oct. 1, 2004, the complete disclosure of which is incorporated herein by reference) can correct for the distortions in the image caused by the differences between the theoretical position of the illumination spot defined by the drive signal and the slower, actual position of the illumination spot, the stored energy in the resonating fiber may also cause a "hole" to appear in the center of the image (FIG. 4). Remapping methods can not correct for the hole in the center of the image. The hole in the center of the image is caused when the drive signal repeats the increasing amplitude portion of the drive signal before the illumination spot can return back to the center of the image (e.g., its initial, center position). In some scenarios, a diameter of the hole may be equal to half of the image, or more.

The second issue also involves the fact that the scan pattern may vary during the increasing amplitude portions and decreasing amplitude portions 17, 19 of the scan pattern 11. Using image or drive remapping and other techniques, however, it is possible to generate images in both scan directions that appear identical. Unfortunately, the actual scan pattern of the illumination spot may change depending on the environmental factors at the site of its use. Typically, temperature has the biggest effect on the scan pattern. For example, on the increasing amplitude portion 17, the changes caused by the higher or lower temperatures may be small and can be ignored or otherwise compensated for with the remapping methods. But for the decreasing amplitude portion 19, the changes caused by the temperature may be harder to correct. The temperature factors may cause images in the two scan directions to change in opposite ways. For example, on the increasing amplitude portion, the image may rotate clockwise, while during the decreasing amplitude portion the image may rotate counter-clockwise. If images are captured during both the increasing and decreasing amplitude portions, this may result in a display in which two diverging images are toggled at the frame update rate, which will cause the resultant captured image to become useless.

Therefore, what are needed are methods and systems which can provide high frame rates while accurately generating an image of the target area. It would be desirable if such methods and system can compensate for the energy stored in the resonating scanning element.

BRIEF SUMMARY OF THE INVENTION

The present invention provides methods and systems for improving a frame rate of a resonant scanning beam device. More specifically, the methods and systems of the present invention are directed at rapidly removing the stored energy and stopping the scanning of the scanning element in a short amount of time.

The methods of the present invention will typically provide a frame rate between about 5 Hz and about 60 Hz, and preferably between about 15 Hz and about 30 Hz. As can be appreciated, the present invention may provide frame rates below or above the aforementioned ranges, and the present invention is not limited to such ranges.

The methods of the present invention are applicable to both one-dimensional and two-dimensional scan patterns. The drive signals for achieving the scan pattern may have similar frequencies in both a horizontal drive axis and a vertical drive axis (e.g., for a spiral scan pattern) or the scan pattern may have different frequencies in the horizontal drive axis and vertical drive axis (e.g., for a propeller scan, raster scan, or the like).

For improved stability and scan repeatability over various environmental conditions, images of the target area are typically only captured during one portion of the drive signal. For example, in a spiral scan pattern, image data is captured only during a first portion of the scan pattern in which an illumination spot is spiraled outward from an initial, center position. A second portion of the scan pattern is used to return the illumination spot to its initial center position. Once the illumination spot returns to the center position, the drive signal can be repeated.

In one aspect, the present invention is directed toward generating and applying a drive signal for the second portion of the scan pattern that is configured to return the illumination spot as rapidly as possible from the end of the first portion of the scan pattern to the initial center point. Reducing the retracing time will allow for an increased number of spiral scans that are devoted to image acquisition.

In one embodiment, the drive signal used to drive the scanning element comprises a first component and a second component. The first component of the drive signal will be used to scan the illumination spot over the target area in the desired scan pattern. The second component of the drive signal will be used to remove stored energy from the scanning element. In one configuration, the second component of the drive signal is a phase braking signal that is phase shifted from the first component of the drive signal. The second component of the drive signal rapidly removes the energy from the scanning element so as to return the scanning element substantially to its zero motion point. Because the scanning element is typically brought to rest at its center point, an image of the target site without holes may be generated.

When the scanning element is driven at resonance, the drive signal and the position of the illumination spot are approximately 180 degrees out of phase. To remove the energy stored in a resonant system, the phase braking signal (e.g., the second component of the drive signal) is forced in phase with the position of the illumination spot. This is accomplished by changing the phase of the horizontal and vertical drive signals from the first component by approximately 180 degrees. This is equivalent to inverting both the Y and Z drive signals.

However, if the phase of the drive signal is kept constant throughout the second component, the changing phase of the position of the scanning element will eventually reach the point where the fiber is driven approximately 90 degrees out of phase and the amplitude will begin to increase. In fact, Applicants have found that anything other than in-phase driving reduces the rate at which energy is removed from the system. For this reason it is desirable to continually adjust the phase of the drive signal such that it remains in phase with the position of the scanning element until substantially all of the energy is removed and motion of the scanning element substantially stops. As soon as substantially all of the energy is removed from the scanning element and the scanning element is substantially motionless, the drive signal will reenergize the scanning element and the scan amplitude will increase.

One exemplary method of determining an appropriate phase braking drive signal or second component of the drive signal is to use a feedback control loop. The feedback control loop (whether real-time or iterative) can be used to determine the appropriate drive signal to quickly remove the energy from the scanning element. The generated drive signal can be recorded in a memory of the system and used as the second component of the drive signal. In alternative embodiments, an operator may manually adjust the phase of the drive signal until all or substantially all of the energy is removed from the scanning element.

In additional aspects, the present invention is directed toward methods and systems for generating and applying a drive signal to a scanning beam device so that the scanning element is caused to scan an illumination spot over a target and then returned to a starting position by using the drive signal to remove kinetic energy from the scanning element. During the period where energy is being removed, a frequency of the drive signal can be selected to match a natural frequency of the scanning element.

Other aspects, objects and advantages of the invention will be apparent from the detailed description that follows.

DETAILED DESCRIPTION OF THE INVENTION

The present invention provides methods and systems for improving a frame update rate of a scanning beam device by rapidly removing stored energy in a scanning element and returning the scanning element to its starting position.

The scanning beam systems of the present invention include a scanning beam device and a base station for controlling the image formation or image acquisition of the scanning beam device. The scanning beam devices of the present invention may take on a variety of forms, but are typically in the form of an endoscope, catheter, fiberscope, microscope, boroscope, bar code reader, an image display, or other devices for generating images or acquiring images of a target area. The scanning beam devices of the present invention may be a limited use device (e.g., disposable device) or a multiple-use device. If the device is for medical use, the scanning beam devices will generally be sterile, either being sterilizable or being provided in hermetically sealed package for use.

The scanning beam devices of the present invention include a scanning element for scanning a beam of light onto a target area. The scanning element preferably comprises a single, cantilevered optical fiber. In other embodiments, the scanning element may take the form of mirrors, such as microelectomechanical system (MEMS), galvanometer, a polygon, multiple optical elements moved relative to each other, or the like. While the remaining discussion focuses on scanning fiber device that is used for acquiring images of a target site, it will be appreciated that the present invention also encompasses the other aforementioned scanning elements and systems.

The methods of the present invention focus on the use of a two-dimensional spiral scan. It should be appreciated however, that the present invention is not limited to such a scan pattern. For example, the present invention may also use other two dimensional scan patterns such as a rotating propeller scan pattern, a raster scan pattern, or a one-dimensional line pattern.

Figure 5:
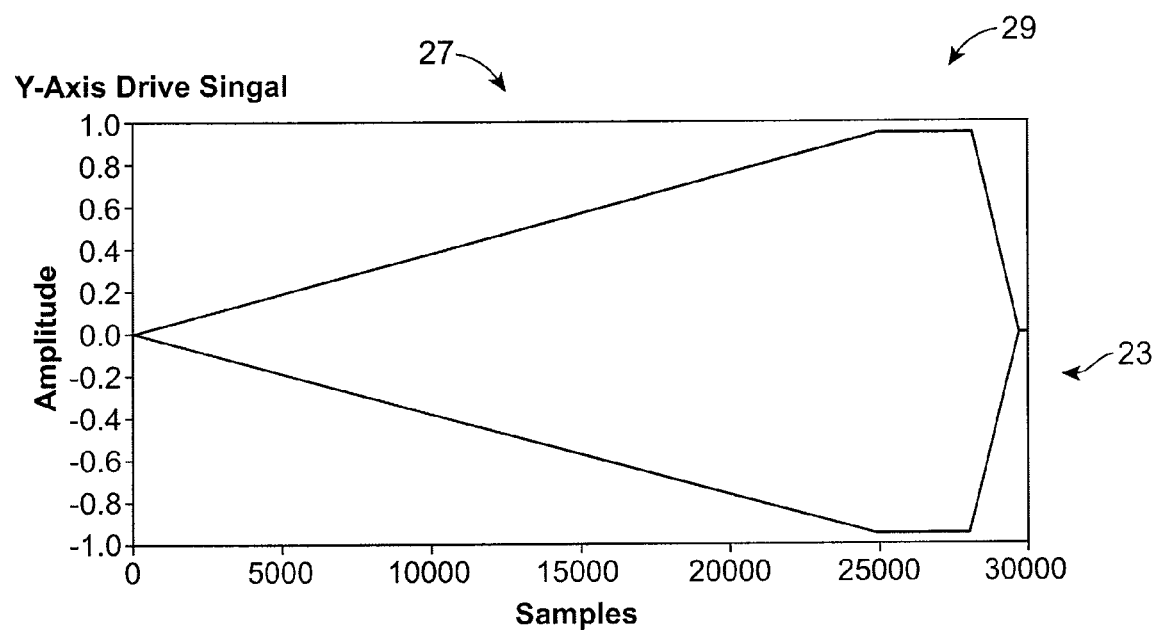
FIG. 5 shows one example of a y-axis drive signal envelope that scans the scanning element in a two dimensional spiral pattern and removes energy from the scanning element to return the scanning element to its starting position.
Figure 8:
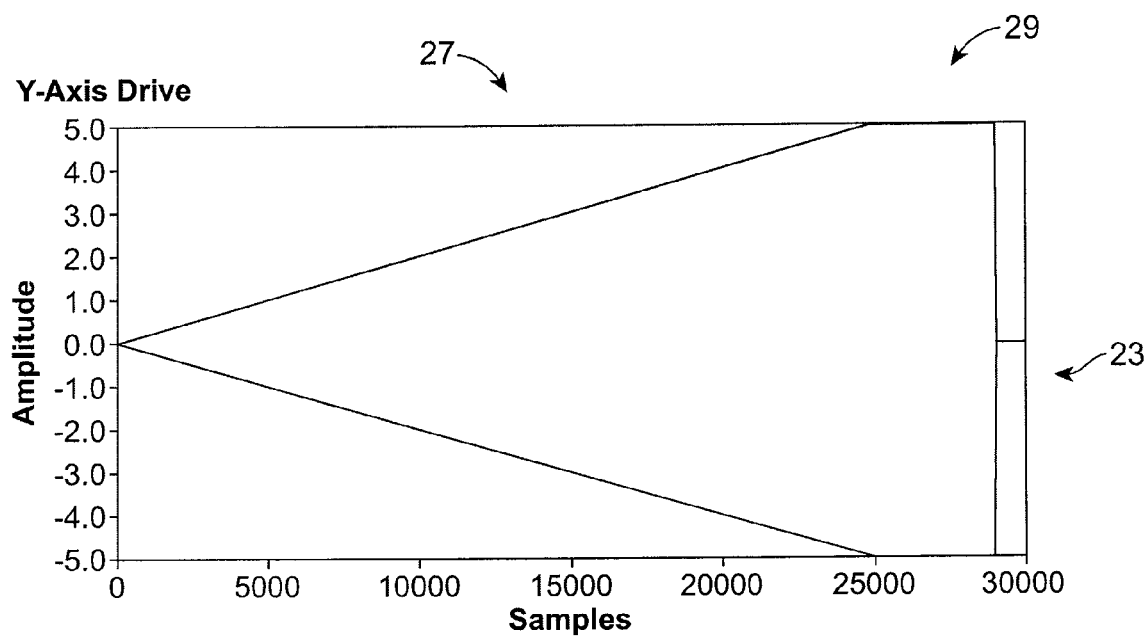
FIG. 8 shows another example of a y-axis drive signal envelope that is encompassed by the present invention.

FIGS. 5 and 8 schematically illustrate two scan envelopes 23 that illustrate some examples of possible amplitudes changes of the drive signal over a single cycle of the scan pattern. For ease of reference, only a drive envelope for the Y-axis drive signal are shown in FIGS. 5 and 8. It should be appreciated however, that for a spiral scan pattern of a round optical fiber, the scan pattern for the y-axis drive signal and the z-axis drive signal will generally have a similar shaped envelope, and the primary difference between the two drive signals 13, 15 (FIG. 2) will be a phase offset of the y-axis and z-axis drive signals within the drive envelope.

The drive signal comprises a first component 27 and a second component 29. An ideal first component 27 of the drive signal will comprise a sinewave that has a linearly increasing amplitude (e.g., the increasing amplitude portion 17). However, drive remapping of the drive signal may change the envelope of the first component of the drive signal and the envelope may not have a linearly increasing amplitude.

Figure 1:
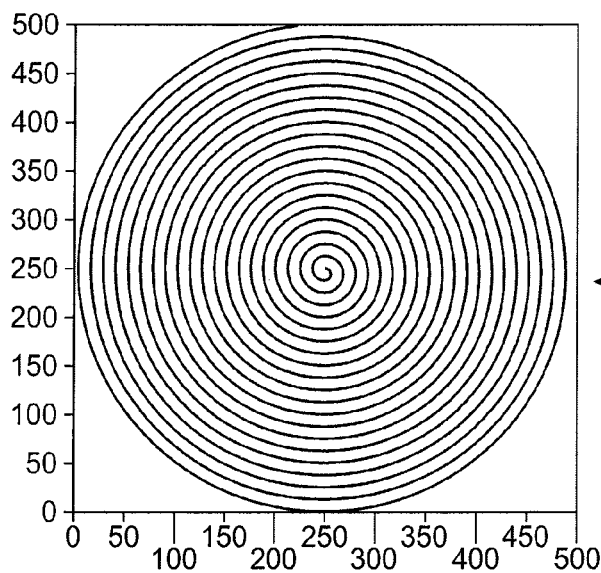
FIG. 1 illustrates an exemplary two-dimensional scan pattern that is encompassed by the present invention.

At the end of first component 27, the illumination spot will have reached the largest diameter of the scan pattern (FIG. 1). After the illumination spot has reached its largest diameter, it is desirable to return the illumination spot and scanning element back to its initial starting point (e.g., the center of the spiral).

Figure 2:
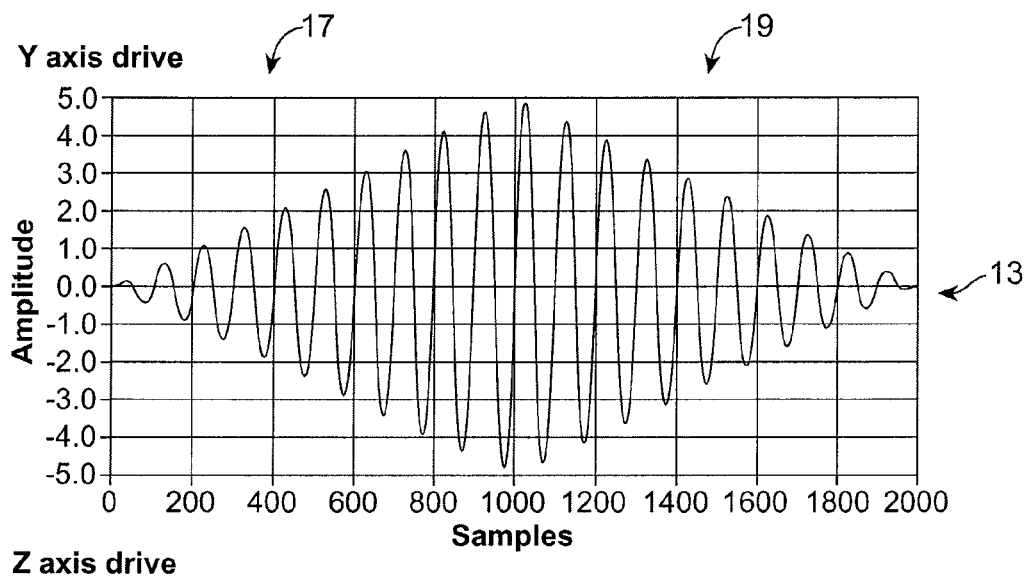
FIG. 2 illustrates one exemplary y-axis drive signal and z-axis drive signal that may be used to generate the scan pattern of FIG. 1.
Figure 2:
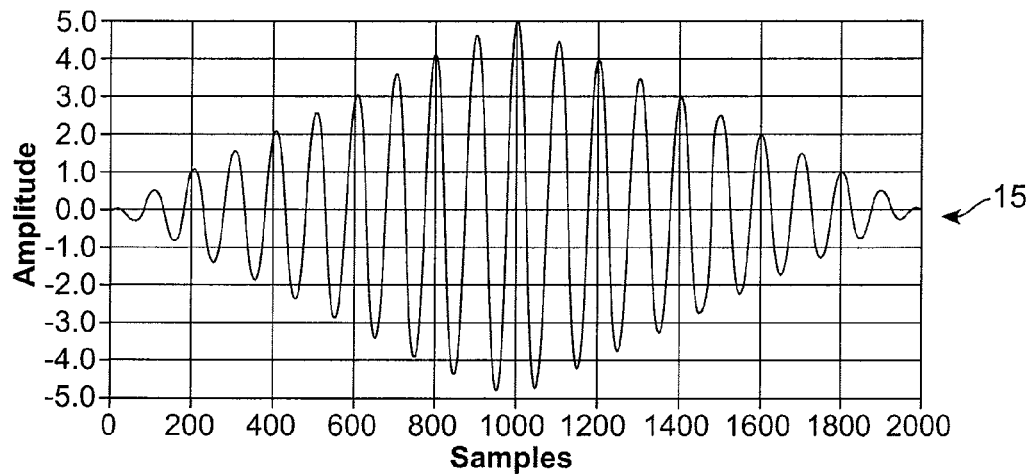

Because of the aforementioned differences of the scan pattern of the illumination spot during the increasing amplitude portion 17 (e.g., the first component 27) and the decreasing amplitude portion 19 of the drive signal (e.g., the second component 29; FIG. 2), data acquisition (e.g., imaging of the target area) will typically occur during only one of the first component 27 of the drive signal and the second component 29 of the drive signal. In a preferred embodiment, imaging of the target area will occur during the spiraling of the illumination spot outward, and no imaging of the target area will occur as the illumination spot is returned substantially to "zero" (e.g., at or near its initial, center position).

Applicants have found that if the drive signal is simply set to "zero," the motion of the illumination spot will exponentially decay toward zero. Unfortunately, the exponential decay takes a considerable amount of time that is not conducive to high frame rates. For example, Applicants found that for a scan pattern that has 250 increasing spirals, it would take over 600 spiral periods for the motion of the illumination spot to settle to zero and return to the initial, center point. However, instead of simply decreasing an amplitude of the sinewave, the present invention applies a "phase braking" second component 29 of the drive signal whose signal has a phase shift relative to the drive signal in the first component 27. In a preferred embodiment, the second component 29 has an inverted phase relative to the first component 27.

Figure 6:
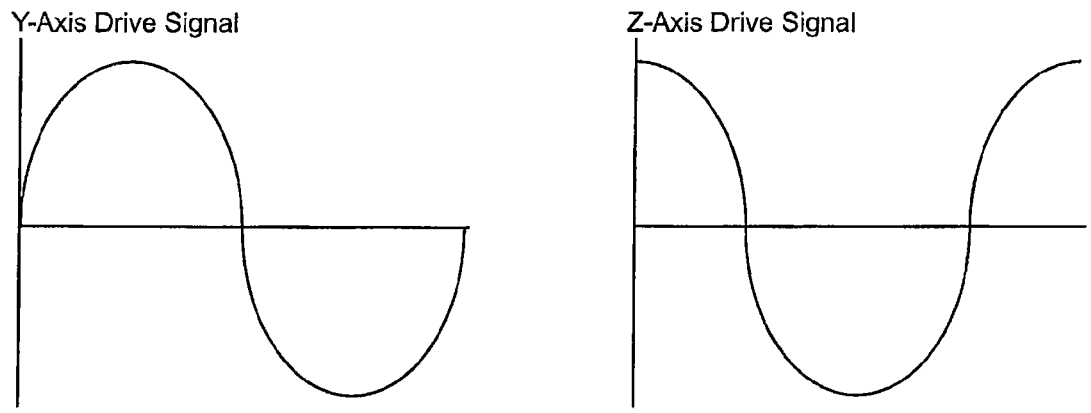
FIG. 6 shows a 90 degree offset between the y-axis drive signal and the z-axis drive signal in a first component of the drive signal.

When the scanning element is scanned at its resonant frequency, the drive signal and the position of the illumination spot are approximately 180 degrees out of phase. To remove the energy stored in the resonating scanning element, the second component 29 of the drive signal is forced into phase with the position of the scanning element. FIG. 6 schematically illustrates y-axis and z-axis drive signals that are used to drive the scanning element during a first component 27 of the drive signal. As shown in FIG. 6, the y-axis drive signal and the z-axis drive signal are 90 out of phase.

Figure 7:
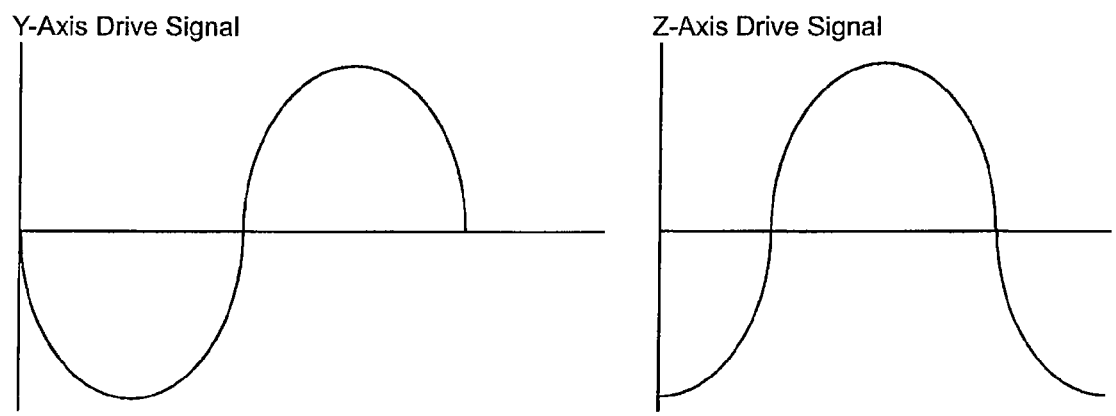
FIG. 7 shows an inverted y-axis drive signal and the z-axis drive signal (compared to FIG. 6) that forms part of the second component of the drive signal.

In a preferred method shown in FIG. 7, the second component 29 of the drive signal is forced into phase with the position of the scanning element by changing the phase of the y-axis drive signal and the z-axis drive signal by approximately 180 degrees. Forcing the y-axis and z-axis drive signal into phase with the position of the illumination spot is equivalent to inverting the y-axis and z-axis drive signals.

The phase braking signal typically has the effect of rapidly reducing the amplitude of the scanning element motion and slightly slowing the frequency of the scanning element. The slowing frequency of the scanning element, however, causes the phase relationship between the drive signal and the position of the scanning element (and illumination spot) to change over time. Applicants have found that it is highly desirable to maintain the second component 29 of the drive signal in phase with the position of the scanning element substantially throughout the second component of the signal. If the phase of the second component of the drive signal is kept constant, the changing frequency and changing position of the scanning element will inevitably reach a point where the scanning element is again 180 degrees out of phase with the signal. When the second component 29 of the drive signal and the position of the scanning element are approximately 90 degrees out of phase with each other, the amplitude of the movement of the scanning element will again begin to increase and energy will again be stored in the scanning element, instead of being removed.

In order to remove the energy from the scanning element, it is desirable to continually adjust the phase of the drive signal so that the drive signal remains in phase with the scanning element until most or all of the energy is removed from the scanning element and the scanning element movement is substantially stopped. Once the energy is removed from the scanning element and the scanning element is positioned substantially back at its initial starting point (e.g., at or near the center of spiral, at or near the center of range of motion, and/or at or near the center of the target area), the drive signal cycle may be repeated and the increasing amplitude first component 27 of the drive signal may again cause the illumination spot to spiral outward in its imaging pattern.

In addition to the phase shift, the drive signal envelope shape of the second component 29 may be optimized to rapidly remove the stored energy from the scanning element and substantially return the scanning element back to zero. Using the phase shifted second component 29 of the drive signal and modified drive signal envelopes described herein, Applicants have been able to remove the stored energy from the scanning element in less than about 50 spiral periods.

FIGS. 5 and 8 illustrate some examples of drive envelopes that may be used as a phase braking driver to remove energy from the scanning element. As shown in FIG. 5, the imaging portion comprises the first component 27 of the drive signal that has the increasing amplitude that extends from sample points 0 to 25000. At sample point 25000, the scanning element reaches its largest desired diameter and the second component 29 of the drive signal is used to remove energy from the scanning element. Thus, at sample point 25000, the phase of both the y-axis and z-axis drive signals are reversed. While not shown in FIG. 5, it should be appreciated that the phase of the second component 29 of the drive signal may be continually adjusted so as to maintain the in phase relationship with the position of the illumination spot.

In addition to changing the phase of the drive signal, the amplitude of the drive signal may also be adjusted during the second component 29 of the signal. In the illustrated example, the amplitude of the drive signal is held constant for a number of sample points (from sample points 25000 to 28000) to quickly remove energy from the scanning element. At sample point 28000, after a majority of the energy has been removed the amplitude of the signal is reduced so as to not re-energize the scanning element. Finally, for a small number of sample points (from sample point 29500 to 30000) the drive signal is set to zero to allow the scanning element motion to substantially settle to zero.

FIG. 8 shows another example of a drive envelope that may be used to remove energy from the scanning element. As shown in FIG. 8 the imaging portion comprises the first component 27 of the drive signal that has a substantially linearly increasing amplitude that extends from sample points 0 to 25000. Similar to FIG. 5, at sample point 25000, the scanning element reaches its largest desired diameter and the second component 29 of the drive signal is used to remove energy from the scanning element. Thus, at sample point 25000, the phase of both the y-axis and z-axis drive signals are reversed. Instead of changing the amplitude of the drive signal, the amplitude is kept constant from sample points 25000 to 29000. At sample point 29000, the drive signal is set to zero to allow the scanning element to substantially settle to zero (e.g., from points 29000 to 30000).

As can be appreciated, the drive envelopes shown in FIGS. 5 and 8 are merely two examples of drive envelopes that may be used to remove energy from the scanning elements of the present invention. The second component 27 may have any combination of a linear or non-linear increasing amplitude, exponentially increasing or decreasing amplitude, a linear or non-linear decreasing amplitude, and/or a zero amplitude, and the amplitudes of the second component 29 of the drive signal will vary according to the specific scanning element and imaging conditions.

Continuous adjusting of the phase to keep the position of the scanning element and the drive signal in phase causes a small change in the frequency of the drive signal. Thus, because phase and frequency are related to each other, instead of adjusting the phase of the drive signal it may be possible to instead adjust a frequency of the drive signal to achieve a similar removal of energy from the scanning element. In such embodiments, it may be desirable to continually adjust the frequency of the drive signal throughout the second component 29 of the drive signal until substantially all of the stored energy is removed from the scanning element.

In configurations in which the drive assembly for the scanning element is a piezoelectric drive assembly, the controller typically generates a voltage drive signal. In such configurations, a polarity of the voltage of the drive signal is changed during the second component 29 of the drive signal to remove energy from the scanning element. If desired, after the voltage polarity is adjusted, the voltage level may be increased to remove the stored energy from the scanning element more rapidly. As can be appreciated, the concepts of the present invention can be used for any types of drive signal (e.g., current signal) and any type of drive assembly, and the present invention is not limited to a voltage drive signal.

Because different scanning elements and drive assemblies will have different characteristics, in order to properly operate the scanning beam system, a customized drive signal for the scanning beam system should be used. The customized drive signal may scan the scanning element at its resonant frequency and may provide an improved scan rate by driving the scanning element with a drive signal that quickly repositions the scanning element back at its zero position after each scan cycle of the target area.

The customized drive signal may be generated using any conventional method, but will typically be generated by manually adjusting the phase of the second component of the drive signal or by using one or more feedback control loops during calibration. The feedback control loops may be real-time or iterative. In one embodiment, a feedback control loop may be used by the manufacturer prior to packaging of the scanning beam device. The feedback control loop may optionally be used to remap an ideal first component of the drive signal so that the illumination spot will follow the ideal scan pattern. Thereafter, the same or different feedback control loop may be used to determine the second component of the drive signal that rapidly removes the energy from the scanning element and moves the scanning element back to zero. Thereafter, the customized drive signal may be stored in a memory in the scanning beam device as an algorithm or look up table.

When the scanning beam device is coupled to a controller, the controller may download the customized drive signal of the particular scanning beam device from the memory. A more complete description of a memory and other data that may be stored on the memory of the scanning beam device is described in commonly owned and copending U.S. patent application Ser. No. 10/956,473, filed Oct. 1, 2004, entitled "Configuration Memory for a Scanning Beam Device", the complete disclosure of which is incorporated herein by reference.

In other configurations, the drive signal may be determined at the imaging site by the operator by calibrating the particular scanning beam element just prior to imaging the target area. For example, the scanning beam element may be placed in a calibration chamber that is coupled to or formed in the base station, and the drive signal may be manually or automatically remapped and calibrated to determine an appropriate first component 27 and second component 29 of the drive signal. Once the drive signal is determined for that specific scanning beam device, the drive signal may be stored as an algorithm or table in a memory of the scanning beam device. Of course, in other embodiments, the customized drive signal may be stored in other computer readable storage elements beside the memory in the scanning beam device. For example, the customized drive signal may be stored in a memory of the controller, a remote database that is accessible by the controller or the like.

Figure 9:
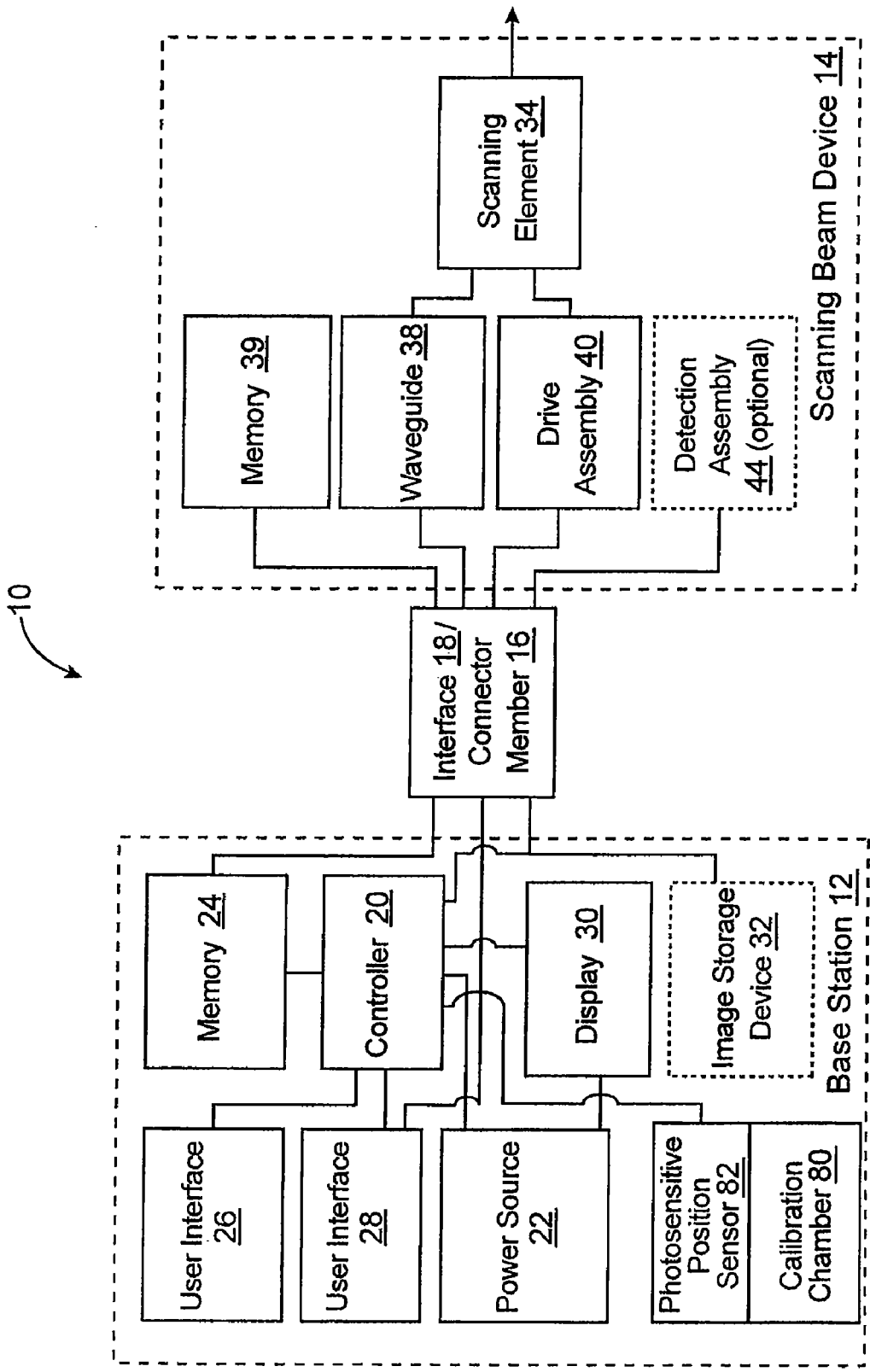
FIG. 9 schematically illustrates a scanning beam system encompassed by the present invention.
Figure 10:
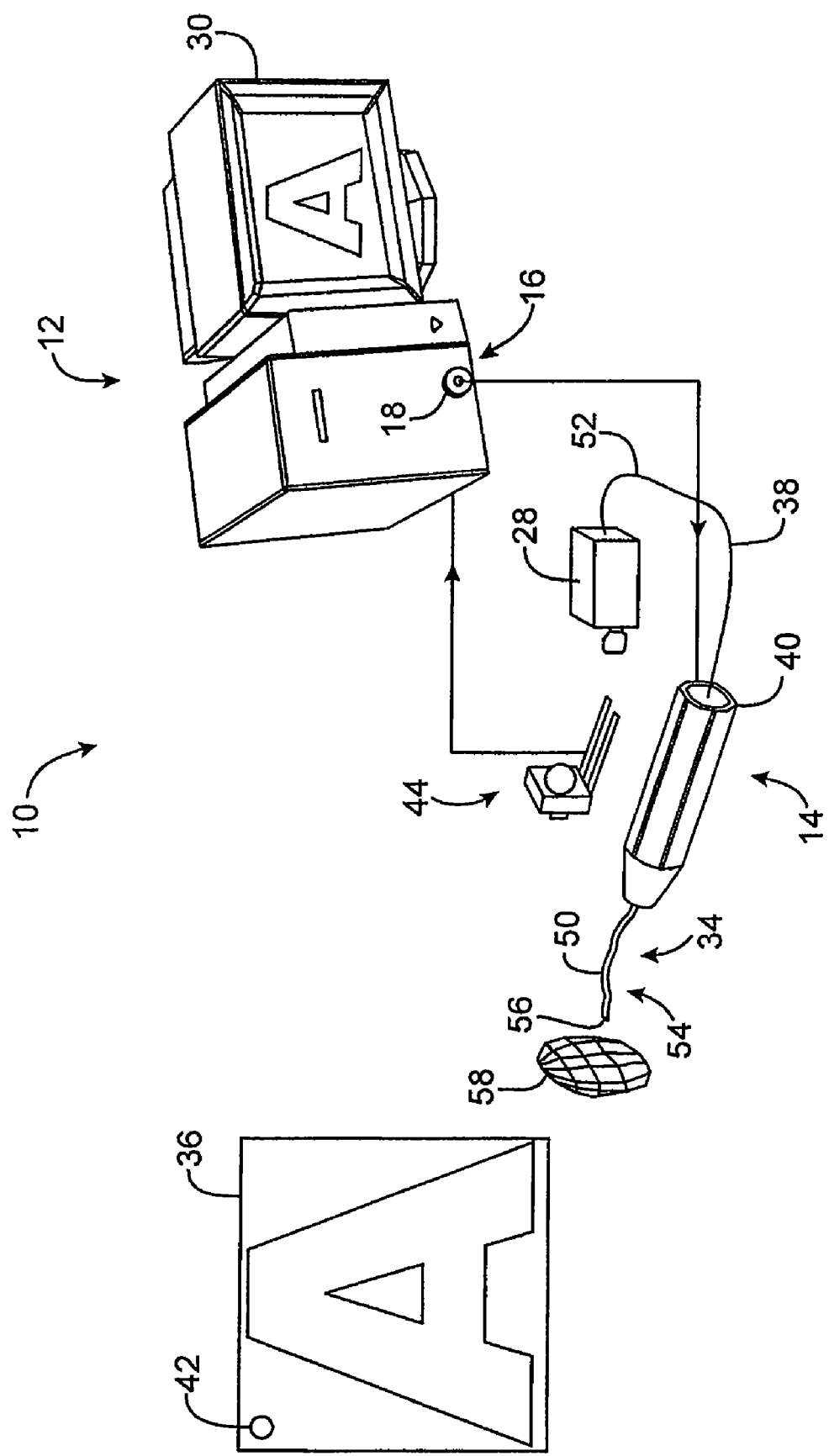
FIG. 10 illustrates a simplified scanning fiber system encompassed by the present invention.

FIGS. 9 and 10 illustrate scanning beam systems 10 that are encompassed by the present invention. The scanning beam system 10 may include a base station 12 and a scanning beam device 14. The scanning beam device 14 includes a connector member 16 that is configured to mate with an input interface 18 on the base station. Coupling of the connector member 16 to the input interface 18 may create a power path, drive signal path, detector path, illumination path, and/or data communication path between elements of the base station 12 and related elements of the scanning beam device 14.

As shown in FIG. 9, base station 12 typically includes a controller 20 that has one or more microprocessors and/or one or more dedicated electronics circuits which may include a gate array (not shown) which may control the actuation of the scanning beam device 14 and generation of the images. The controller 20 may also include scanner drive electronics, detector amplifiers and A/D converters (not shown). The drive electronics in the controller and the software modules stored in memory are used to provide a customized control routine for the scanning beam device 14. The methods of the present invention may be implemented with hardware, software, firmware, specialized circuitry, specialized processors, or a combination thereof. In embodiments, in which the methods are carried out as software, the software is preferably implemented as an application program in the form of a plurality of software modules that are tangibly embodied in a memory of the system or on other computer readable medium. While the remaining discussion focuses on a software implementation of the methods of the present invention, it should be appreciated that the present invention is not limited to the software implementation.

Controller 20 is in communication with a plurality of elements within the base station 12 via a communication bus (not shown). The communication bus typically allows for electrical communication between controller 20, a power source 22, memory 24, user interface(s) 26, one or more light sources 28, one or more output displays 30, and a photosensitive position sensor 82. Optionally, if the scanning beam device 14 includes a detection assembly, the base station 12 may include a separate image storage device 32 in communication with controller 20. In alternative embodiments, the image storage device 32 may simply be a module within memory 24. As can be appreciated, the base stations 12 of the present invention will vary, and may include fewer or more elements than illustrated in FIG. 9.

Depending on the particular scanning beam device 14 used, the light source 28 may emit a continuous stream of light, modulated light, or a stream of light pulses. Base station 12 may comprise a plurality of different light sources 28 so as to be able to operate different scanning beam devices that have different illumination capabilities. The light sources 28 may include one or more of a red light source, blue light source, green light source (collectively referred to herein as a "RGB light source"), an IR light source, a UV light source, and/or a high intensity laser source (typically for a therapeutic scanning beam device). The light sources 28 themselves may be configured to be switchable between a first mode (e.g., continuous stream) and a second mode (e.g., stream of light pulses). For ease of reference, other conventional elements in the light source are not shown. For example, if a RGB light source is used, the light sources may include a combiner to combine the different light before it enters the optical fiber 50. Furthermore, while light source 28 is illustrated in FIG. 10 as being separate from base station 12, it should be appreciated that in other embodiments, light sources 28 may be integrated within base station 12.

Memory 24 may be used for storing the software modules that carry out the methods of the present invention, look-up tables, and algorithms that control the operation and calibration of the scanning beam device 14. The control routine used by the controller 20 for controlling the scanning beam device 14 will typically be configurable so as to match the operating parameters of the attached device (e.g., resonant frequency, voltage limits, zoom capability, color capability, etc.). As noted below, memory 24 may also be used for storing the image data received from the detectors 46 of the scanning beam device, image remapping look-up tables and algorithms, remapped drive signals that comprise the first component 27 and second component 29, parameters of the fiber scanning device, etc.

For ease of reference, other conventional elements in the base station 12 are not shown. For example, embodiments of the base stations 12 of the present invention will typically include conventional elements such as amplifiers, D/A converters and A/D converters, clocks, waveform generators, and the like.

The scanning beam devices 14 of the present invention includes a scanning element 34 for delivering and scanning a beam of light onto a target area 36. A waveguide 38, typically in the form of an optical fiber, is optically coupled to the light source(s) so as to deliver illumination from the light source 28 to the scanning element 34. A driving assembly 40 is coupled to the scanning element 34 and is adapted to actuate the scanning element 34 according to a drive signal received from the controller 20. Optionally, the scanning beam device 14 may include a non-volatile memory 39 for storing identification data or parametric data of the scanning beam device 14.

In a preferred embodiment, the scanning element 34 is a cantilevered optical fiber 50. The optical fiber 50 will comprise a proximal portion 52 and a distal portion 54 that comprises a distal tip 56. Optical fiber 50 is typically fixed along at least one point of the optical fiber so as to be cantilevered such that the distal portion 54 is free to be deflected. In such an embodiment, the proximal portion 52 of the optical fiber is the waveguide 38 and will transmit light from light source 28. As can be appreciated, in other embodiments, a separate waveguide 38 may be optically coupled to the proximal portion 52 of the optical fiber so that light from light source 28 will be directed into the optical fiber 50 and out of the distal tip 56.

The optical fiber 50 may have any desired dimensions and cross-sectional shape. The optical fiber 50 may have a symmetrical cross sectional profile or an asymmetrical cross-sectional profile, depending on the desired characteristics of the device. An optical fiber 50 with a round cross-section will have substantially the same resonance characteristics about any two orthogonal axes, while an optical fiber with an asymmetric cross section (e.g., ellipse) will have different resonant frequencies about the major and minor axes. If desired, the optical fiber 50 may be linearly or non-linearly tapered.

Figure 3:
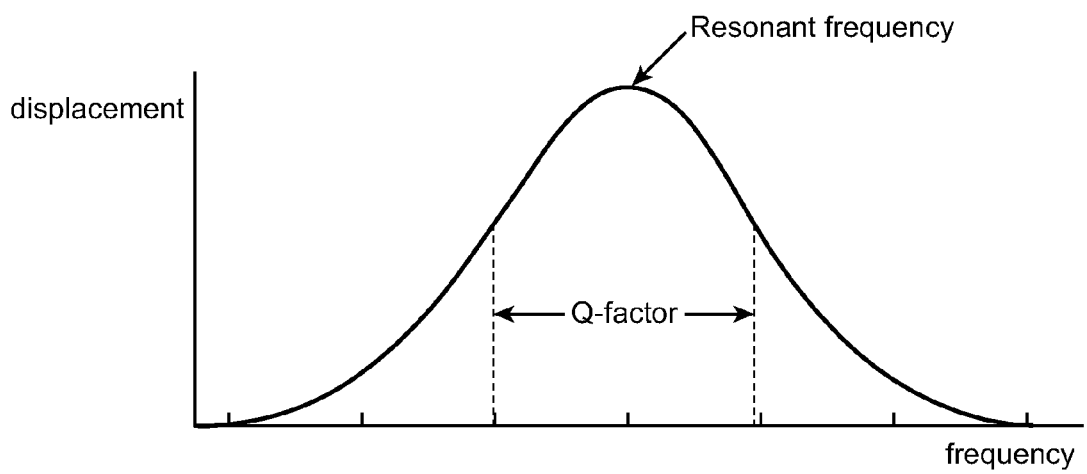
FIG. 3 illustrates a Q-factor of a resonant frequency.
Figure 4:
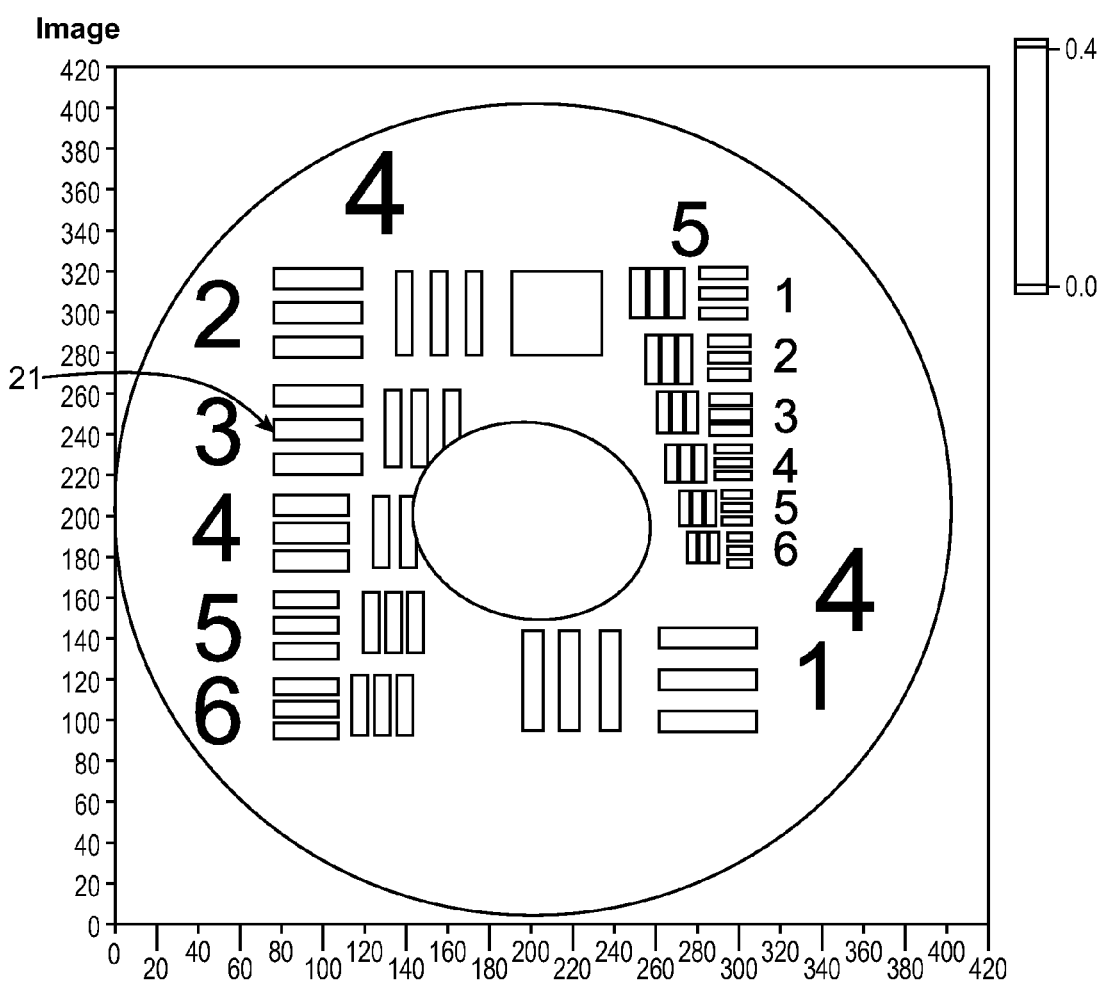
FIG. 4 illustrates an image of a target area that has a hole in a center.

To achieve the deflection of the distal portion 54 of the optical fiber, the cantilevered distal portion 54 of the optical fiber 50 will be coupled to drive assembly 40. As shown in FIG. 3, drive assembly 40 will typically drive the cantilevered distal portion 54 within a Q-factor of the resonant frequency, and preferably at its mechanical or vibratory resonant frequency (or harmonics of the resonant frequency) in a one or two dimensional scan pattern. As can be appreciated, the scanning element 34 does not have to be driven at substantially the resonant frequency, but if the scanning element 34 is not scanned at its resonant frequency, a larger amount of energy will be required to provide the desired radial displacement for the scan pattern. In one preferred embodiment, the drive assembly is a piezoelectric driving assembly. A drive signal from controller 20 delivers a desired signal to the drive assembly 40. The drive signal causes the piezoelectric drive assembly to deflect the distal tip 56 of the optical fiber 50 so that the illumination spot is moved in a desired scan pattern. While preferred drive assemblies are piezoelectric assemblies, in alternative embodiments, the drive assembly 40 may comprise a permanent magnet, a electromagnet, an electrostatic drive, a sonic drive, an electromechanical drive, or the like.

Referring again to FIG. 10, the scanning beam device 14 may optionally comprise one or more lenses 58 near the distal end of the optical fiber 50 to focus the imaging light, to provide better resolution, and/or an improved FOV. The lenses 58 may be coupled to an outer housing (not shown) of the scanning fiber device 14 and fixed relative to the scanning distal end 56 of the optical fiber and/or the lens 58 may be movable relative to the housing (not shown).

A detection assembly 44 may comprise one or more detectors that are in communication with the controller. The detectors are typically coupled to the controller through an amplifier and A/D converter (not shown). The controller (or drive electronics within the controller) may provide a synchronization pulse to provide a timing signal for the data acquisition by the detection assembly 44. Additionally or alternatively, a separate clock circuit (not shown) may be used to correspond the detected light to the time points in the scan pattern. The detection assembly 44 may be disposed anywhere on or within the housing of the scanning fiber device, but will typically be positioned adjacent the distal portion 54 of optical fiber 50 so as to capture backscattered light reflected off of the target area 36. The detection assembly 44 may comprise one of more individual detectors to receive light backscattered from the target area 36. For example, the detection assembly may comprise a light detector (such as a photodetector) that produces electrical signal that are conveyed through leads (not shown) to the base station 12. Alternatively, the detection assembly 44 may comprise one or more collector fibers (not shown) that transmit light reflected from the target area to photodetectors in the base station 12.

The calibration methods for determining the first and second component of the drive signal may be carried out in a calibration chamber 80 shown schematically in FIG. 9. Calibration chamber 80 may be formed as part of the base station 12, it may be separate from the base station 12, or it may be incorporated as part of the manufacturer's test equipment (not shown). Calibration chamber 80 may be used during a calibration step to (1) determine the resonant frequency of the scanning fiber, (2) to remap the first component of the drive signal, and (3) to determine and optimize the second component 29 of the drive signal to remove the stored energy from the scanning fiber.

Calibration chamber 80 may be environmentally controlled so as to match the anticipated environments of the scanning fiber devices. Calibration chamber 80 will be sized to receive at least a distal portion of the scanning fiber device 14 and may have a holder (not shown) that positions the scanning fiber device substantially in a center of the calibration chamber 80. Calibration chamber 80 will typically have a light detector coupled to the controller. The light detector is preferably a position sensitive detector (PSD) 82 that captures the position of the illumination spot during the scan pattern. In use, the controller will be configured to initiate the scanning pattern. Analog signals from the PSD 82 will be sent to the dedicated, specialized hardware electronics in the controller through an A/D converter (not shown) and the controller will correspond the position data with the time points of the scan pattern. Optionally, the calibration chamber may have a temperature controller and a temperature sensor coupled to the controller. Controller may be configured to measure and/or adjust the temperature of the calibration chamber before or after the characterization of the scan pattern of the scanning fiber device.

Because the characteristics of the scanning fiber device 14 may operate differently in different operating modes (e.g., different zoom levels, etc.) or operate differently in different environmental conditions (e.g., temperature, etc.), separate look-up tables or algorithms may be generated when the scanning fiber device is in the calibration chamber 80 for some or all of the selected operation modes and/or environmental conditions. If only selected operation modes or environmental conditions are used to generate a look up table, the controllers of the present invention may be configured to interpolate between the generated look-up tables and algorithms to generate look-up tables for other modes and conditions.

For example, in one configuration, there may be separate look-up table for different zoom levels. Zoom is generally accomplished by reducing the maximum drive voltage delivered to the drive assembly 40 so as to reduce the amplitude of the scanning. However, the different voltages could provide different positional differences other than simple amplitude changes in the optical fiber and illumination spot. As such, it may be desirable to have different look-up tables for the different zoom levels. The zoom capability may be limited to specific zoom levels so that memory is not overloaded with a large number of look-up tables or algorithms. It may be possible to provide a predetermined number of look-up tables for a predetermined spaced zoom levels and any non-characterized zoom level between the predetermined zoom levels may have a look-up table generated by the controller by interpolating between the spaced zoom tables.

Additionally, there may be different first components and second components of the drive signals for the different anticipated environmental conditions. For example, the memories in the system 10 may comprise look-up tables or algorithms for a variety of different temperatures or temperature ranges. In such embodiments, the scanning fiber device 14 may comprise a temperature sensor (not shown) that is configured to measure the temperature adjacent the distal tip 56 of the optical fiber 50 and configured to send a temperature signal to the controller so that the controller will know which look-up table or algorithm to use. Similar to the zoom tables, it may be desirable to only generate look-up tables for two or more temperatures or temperature ranges. The look-up tables for the two or more temperatures may thereafter be interpolated to generate the look-up tables for the remaining temperatures or temperature ranges.

To acquire an image of a target area 36 with the scanning fiber device 14, light is delivered from light source 28 through the waveguide 38 and projected out of the distal end 56 of the optical fiber so as to form an illumination spot 42 on the target area 36. A first component 27 of the voltage drive signal (either the ideal signal or the remapped drive signal) is delivered through the power source so that the piezoelectric drive assembly 40 vibrates the optical fiber substantially at its resonant frequency and scans the illumination spot in a two-dimensional spiral scan pattern over the target area 36. Backscattered light from the target is sequentially collected by the detection assembly 44 and its collection times are synchronized with its time point in the spiral scan pattern. Based on the known position of the illumination spot at all points of the scan pattern, the sequentially collected light may then be placed in a pixel position that corresponds to the position of the illumination spot at that particular time of the scan pattern to construct an image of the target area one pixel at a time. Once the illumination spot has reached its outer diameter, the second component 29 of the drive signal is delivered to remove the stored energy from the optical fiber and to return the optical fiber to its zero position.

Figure 11:
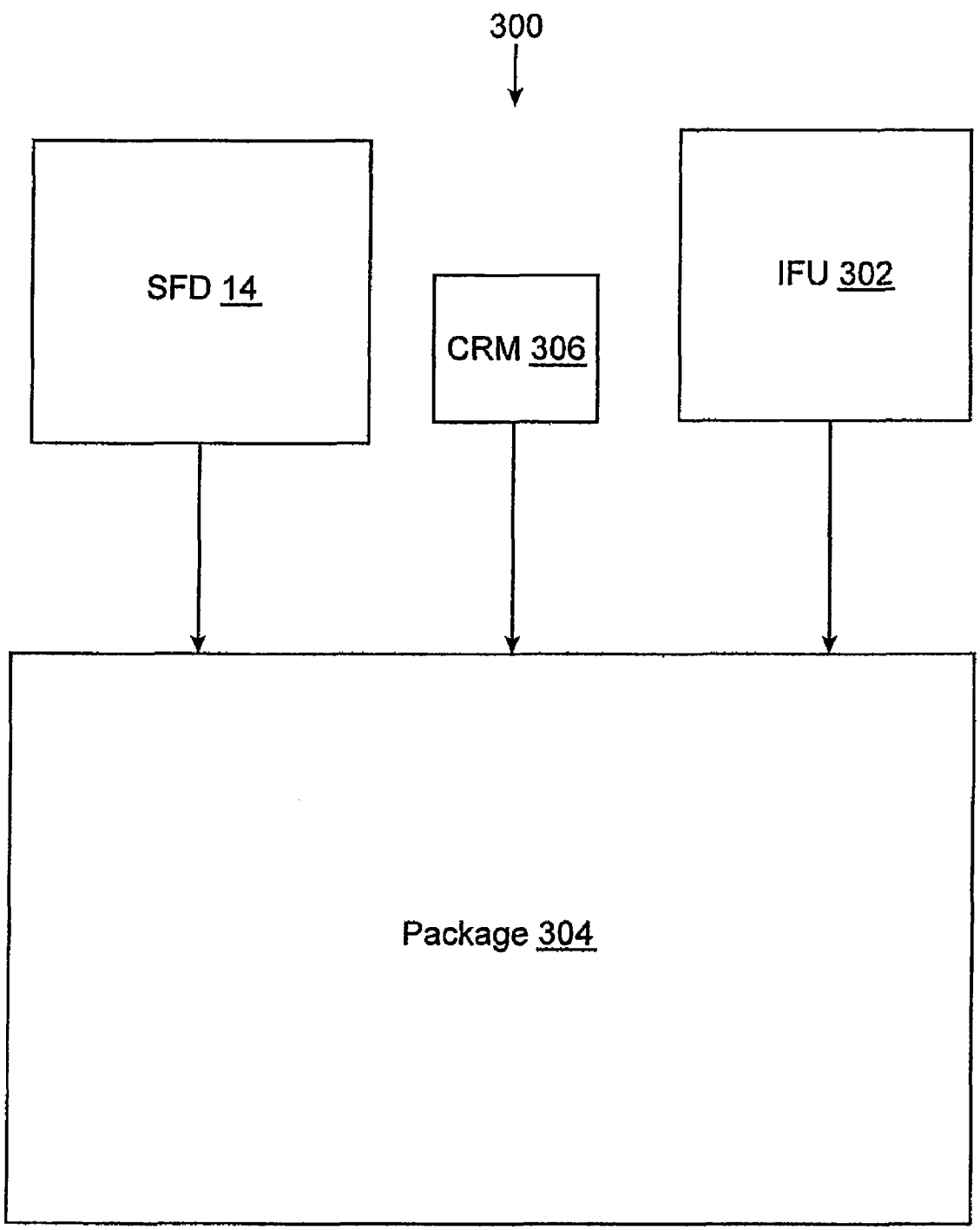
FIG. 11 schematically illustrates a kit encompassed by the present invention.

Referring now to FIG. 11, the present invention also encompasses kits 300. The kit 300 may include a scanning fiber device (SFD) 14 (such as an endoscope), instructions for use (IFU) 302, and at least one package 304. Optionally, the kit 300 may include a computer readable medium (CRM) 306 that is integral with the SFD 14 (such as the non-volatile memory 39) or separate from the SFD (e.g., CD, DVD, floppy disk, etc.)

The scanning fiber device 14 will generally be as described above, and the instruction for use (IFU) 302 will set forth any of the methods described above. Package 304 may be any conventional device packaging, including pouches, trays, boxes, tubes, or the like. IFU 302 will usually be printed on a separate piece of paper, but may also be printed in whole or in part on a portion of the package 304.

The scanning fiber devices may comprise a memory 39 that comprises a look-up table that provides a modified drive signal that comprises the first component for scanning the optical fiber over the target area and second component for quickly removing stored energy from the optical fiber and/or other parametric information regarding the scanning fiber device. Alternatively, a separate computer readable medium 306 may comprise the customized look-up table or algorithm for the drive signal, and/or the parametric data of the scanning fiber device.

As set forth above, the present invention can include rapidly removing the stored energy and stopping the scanning of the scanning element in a short amount of time by coordinating the second component of the drive signal with the movement of the scanning element. An undriven scanning element tends to oscillate approximately at its natural frequency, which can vary with oscillation amplitude. Increased levels of coordination between the frequency and phase of the second component of the drive signal and the movement of the oscillating scanning element can provide for increased energy removal rates. In order to better coordinate the second component with the movement of the scanning element, the second component can be changed or varied during the energy removal period to better match the instantaneous movement frequency of the scanning element.

Increased coordination between the second component of the drive signal and the movement of the scanning element can be achieved using a variety of ways. In one approach, the frequency of the second component is chosen to match a natural frequency of the scanning element. Further, to better match the changing movement frequency of the scanning element that occurs as the amplitude of oscillation changes, the frequency of the second component may be changed one or more times. In a further approach, the frequency of the second component is continually varied so as to match the continually varying movement frequency of the scanning element that results due to changes in its natural frequency with changing amplitude of oscillation. Additionally, as discussed above, the amplitude of the second component may be varied in a variety of ways, for example, by changing the amplitude one or more times or even continually varying the amplitude. Changes to the amplitude of the second component may be made independent of changes to the frequency of the second component.

An additional feature of the present invention relates to the use of drive signals comprising separate components about two separate axes. As discussed above, the drive signal can be comprised of a y-axis component and a z-axis component. In the case of a spiral scan pattern of a scanning element with perfectly symmetrical vibratory characteristics, both the y-axis component and the z-axis component may be sinusoidal in nature and typically 90 degrees out of phase. However, in reality, even nominally symmetrical scanning elements have some level of difference in vibratory characteristics about different axes, such as slight differences in natural frequencies at any one particular amplitude. Further, as discussed above, scanning element natural frequency may vary with amplitude. Accordingly, it can be beneficial to account for these differences in vibratory characteristics by individually tailoring the y-axis and z-axis components, such that the y-axis and z-axis components have their own frequency profile. Such individual tailoring can involve changing each component's frequency one or more times as discussed above, or even continuously varying each component's frequency. At least where the y-axis and z-axis components have been individually tailored, such as having different frequencies at some point in time, the phase angle between the y-axis and z-axis components of the drive signal may be something other than 90 degrees at any particular point in time. Additionally, as discussed above, the amplitudes of the y-axis and z-axis components respectively may be individually tailored independent from the tailoring of the frequencies of the y-axis and z-axis components.

It is understood that the examples and embodiments described herein are for illustrative purposes only and that various modifications or changes in light thereof will be suggested to persons skilled in the art and are to be included within the spirit and purview of this application and scope of the appended claims. For example, while the first component 27 and the second component 29 of drive signal are illustrated and described as different portions of a single signal, in alternative embodiments, the first component 27 and the second component 29 can be formed of two separate signals. Moreover, while the above description focuses on image acquisition, the above systems and methods are equally applicable to image displays. Finally, while most embodiments of the present invention prefer to remove the hole from the image, it may be desirable to not remove all of the stored energy from the scanning element and to leave the hole in the image. Consequently, a majority, but not all, of the energy may be removed from the scanning element, and the scanning element will only "substantially" return to its starting/initial point. Numerous different combinations are possible, and such combinations are considered to be part of the present invention.

What is claimed is:

1. A method of driving a scanning beam device that comprises an optical fiber scanning element, the method comprising:

providing the scanning element in a first position;

driving the scanning element, at a frequency within a Q-factor of the scanning element's resonant frequency, with a first component of a drive signal to scan an illumination spot in a scan pattern over a target; and driving the scanning element with a second component of the drive signal to remove stored energy from the scanning element so as to cause the scanning element to substantially return to the first position, the second component comprising a frequency that corresponds to a natural frequency of the scanning element.

2. The method of claim 1, wherein the second component comprises at least two different frequencies.

3. The method of claim 2, wherein the at least two frequencies substantially correspond with the scanning element's movement frequency at two or more different times during application of the second component.

4. The method of claim 2, wherein the second component comprises a plurality of frequencies with each frequency substantially corresponding with different movement frequencies of the scanning element during energy removal.

5. The method of claim 1, wherein the second component comprises a first-axis signal and a second-axis signal, where at least one point in time exists where the frequency of the first-axis signal is different than the frequency of the second-axis signal.

6. A scanning beam system comprising:
   a scanning beam device comprising an optical fiber scanning element coupled to a drive assembly; and
   a base station coupleable to the drive assembly of the scanning beam device, the base station being adapted to deliver a drive signal to the drive assembly to drive the scanning element,
   wherein the drive signal comprises:
   a first component that is configured to scan an illumination spot emitted from the scanning element from a starting position in a scan pattern and to drive the scanning element at a frequency within a Q-factor of a resonant frequency; and
   a second component that is configured to remove stored energy from the scanning element so as to return the scanning element to the starting position, the second component comprising a frequency corresponding to a natural frequency of the scanning element.

7. The system of claim 6, wherein the second component comprises at least two different frequencies.

8. The system of claim 7, wherein the at least two different frequencies substantially correspond with the scanning element's movement frequency at two or more different times during application of the second component.

9. The system of claim 7, wherein the second component comprises a plurality of frequencies with each frequency substantially corresponding with different movement frequencies of the scanning element during energy removal.

10. The system of claim 6, wherein the second component comprises a first-axis signal and a second-axis signal, where at least one point in time exists where the frequency of the first-axis signal is different than the frequency of the second-axis signal.

* * * * *